(12) United States Patent  (10) Patent No.: US 7,874,598 B2
Chung  (45) Date of Patent: Jan. 25, 2011

(54) AUTO LATCH FOR WINDOW SASH (76) Inventor: Stanley Chung, 5430 Shannon ridge La., San Diego, CA (US) 92130

( * ) Notice: Subject to any disclaimer, the term of this patent is extended or adjusted under 35 U.S.C. 154(b) by 891 days.

(21) Appl. No.: 11/669,166

(22) Filed: Jan. 31, 2007

(65) Prior Publication Data

US 2008/0179896 A1 Jul. 31, 2008

(51) Int. Cl.
*E05C 1/08* (2006.01)
(52) U.S. Cl. .................. 292/163; 292/169; 292/175
(58) Field of Classification Search ................. 292/163, 292/32, 137, 156, DIG. 20, DIG. 31, DIG. 12, 292/DIG. 26, DIG. 61, DIG. 35, DIG. 47; 70/89, 90
See application file for complete search history.

(56) References Cited

U.S. PATENT DOCUMENTS

| | | | | |
|---|---|---|---|---|
| 2,714,030 A | * | 7/1955 | Gardner | 292/178 |
| 4,061,370 A | * | 12/1977 | Hauber | 292/175 |
| 7,097,214 B2 | * | 8/2006 | Tsai | 292/157 |
| 7,261,342 B2 | * | 8/2007 | Smith | 292/332 |
| 7,407,199 B2 | * | 8/2008 | Richardson | 292/163 |
| 2006/0033345 A1 | | 2/2006 | Richardson | |
| 2006/0038413 A1 | * | 2/2006 | Rebel et al. | 292/165 |
| 2008/0129054 A1 | * | 6/2008 | Tremble et al. | 292/33 |

* cited by examiner

*Primary Examiner*—Carlos Lugo
*Assistant Examiner*—Kristina R Fulton
(74) *Attorney, Agent, or Firm*—Patent Law Group LLP; David C. Hsia (57) ABSTRACT

A latch for a window sash includes a fixed plate and a latch head slidably coupled to the fixed plate. The latch head is symmetrically spring loaded to minimize rotation when the latch head translates. When the latch head retracts toward the fixed plates, hooks from the latch head engage notches on the fixed plate to lock the latch head in a retracted position. This releases the latch head from a strike so the window sash can be opened. The latch further includes a plunger centrally received in the fixed plate and the latch head. When the plunger retracts toward the fixed plate, sloped shoulders from the plunger disengages the hooks of the latch head from the notches on the fixed plate. This releases the latch head to engage the strike so the window sash is locked.

14 Claims, 11 Drawing Sheets

AUTO LATCH FOR WINDOW SASH

FIELD OF INVENTION

This invention relates to latches for window sashes and other opening fixtures.

DESCRIPTION OF RELATED ART

Window latches are used to lock sliding window sashes in window frames. Self-latching devices automatically latch the window sashes after the window sashes are closed. To open such a window, the user has to use one hand to unlock the self-latching device and another hand to slide window. Thus, what is needed is an improved self-latching device.

SUMMARY

In one embodiment of the invention, a latch for a window sash includes a fixed plate, a latch head that translates relative to the fixed plate, and a plunger that translates through the latch head and the fixed plate. The fixed plate defines a first passage and notches about the first passage. The latch head includes first and second halves defining a second passage there between. The two halves are equally spring loaded to minimize rotation of the latch head when it translates. The two halves further include hooks for engaging the notches of the fixed plate to lock the latch head in a retracted position. The plunger is spring loaded and centrally received in the first and the second passages of the fixed plate and the latch head. The plunger includes sloped shoulders for disengaging the hooks of the latch head from the notches of the fixed plate to release the latch head from the retracted position.

To open the window sash, a user retracts the latch head to release the latch head from a strike. As the latch head translates toward the fixed plate, its hooks engage the notches of the fixed plate and lock the latch head in a retracted position. This clears the latch head but not the plunger from the strike. When the plunger contacts the strike, it slides toward the fixed plate and its shoulders disengage the hooks of the latch head from the notches of the fixed plate. This action releases the latch head from the fixed plate so that the latch head is extended.

To close the window sash, the latch head and the plunger retract when they contact the strike. The retraction of the plunger ensures that the latch head is released from the fixed plate to lock onto the strike after the latch head and the plunger clear the strike.

BRIEF DESCRIPTION OF THE DRAWINGS

Use of the same reference numbers in different figures indicates similar or identical elements.

DETAILED DESCRIPTION OF THE INVENTION

Figure 1:
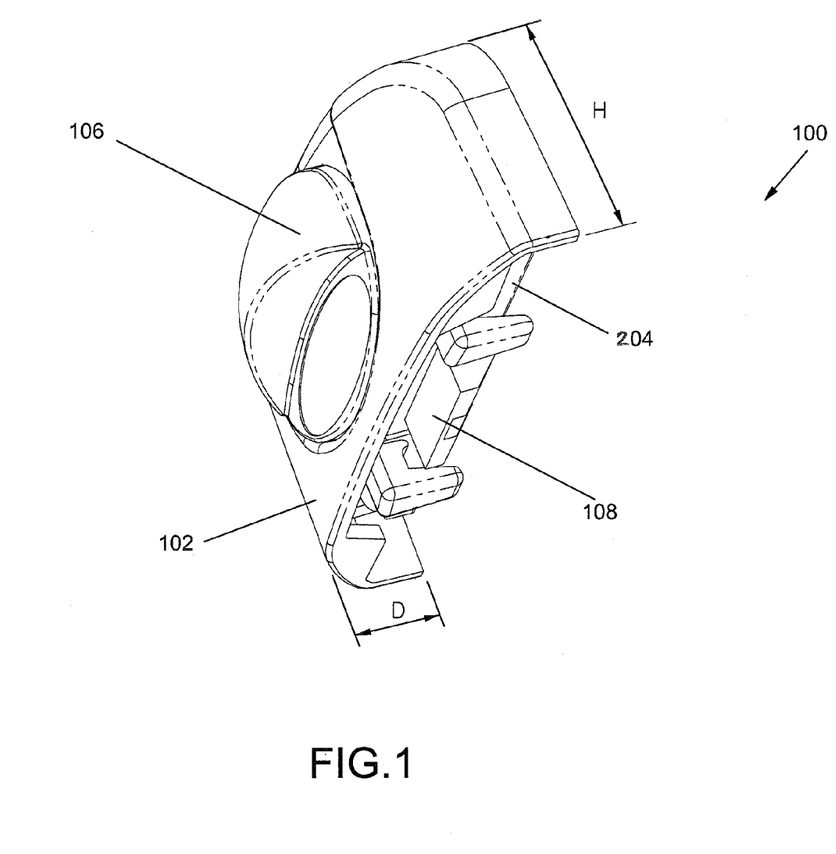
FIG. 1 is a perspective assembled view of a window latch in one embodiment of the invention.

FIG. 1 illustrates an assembled view of a latch 100 for a window sash in one embodiment of the invention. Latch 100 is designed to automatically lock the window sash (not shown) to a strike (not shown) when the window sash is closed. The strike is mounted an opposing part of the window sash or the window frame.

Latch 100 has a cover 102 mounted to a base 104. A trigger 106 is located on cover 102 to unlock the window sash by releasing a latch head 204 from the strike. The height H of cover 102 may be increased to hide the strike so any striker misalignment is not visible. The depth D of latch 100 may be reduced to accommodate a narrow check rail of the window.

Figure 2A:
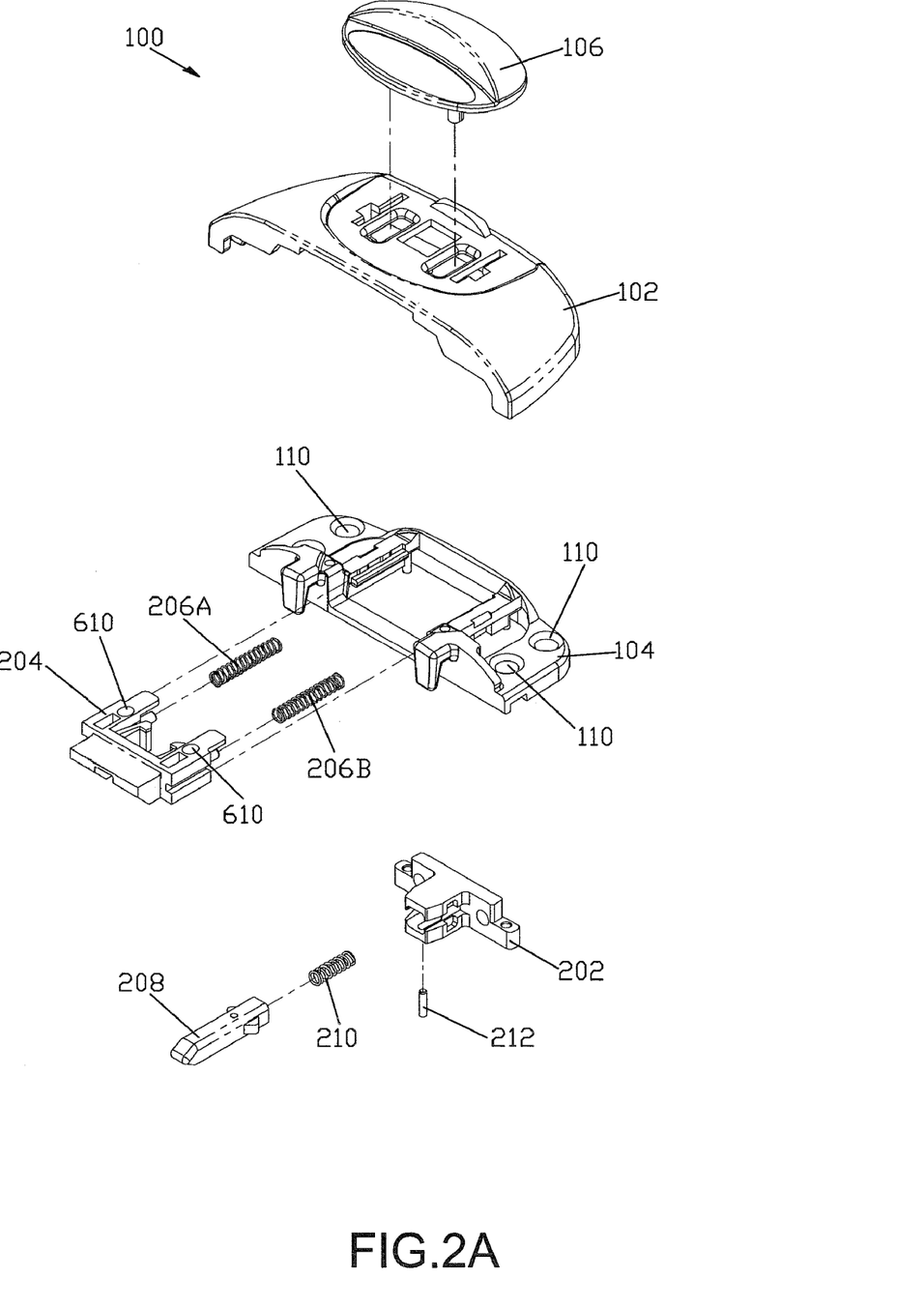
FIGS. 2A and 2B are perspective exploded views of the latch of FIG. 1 in one embodiment of the invention.
Figure 2B:
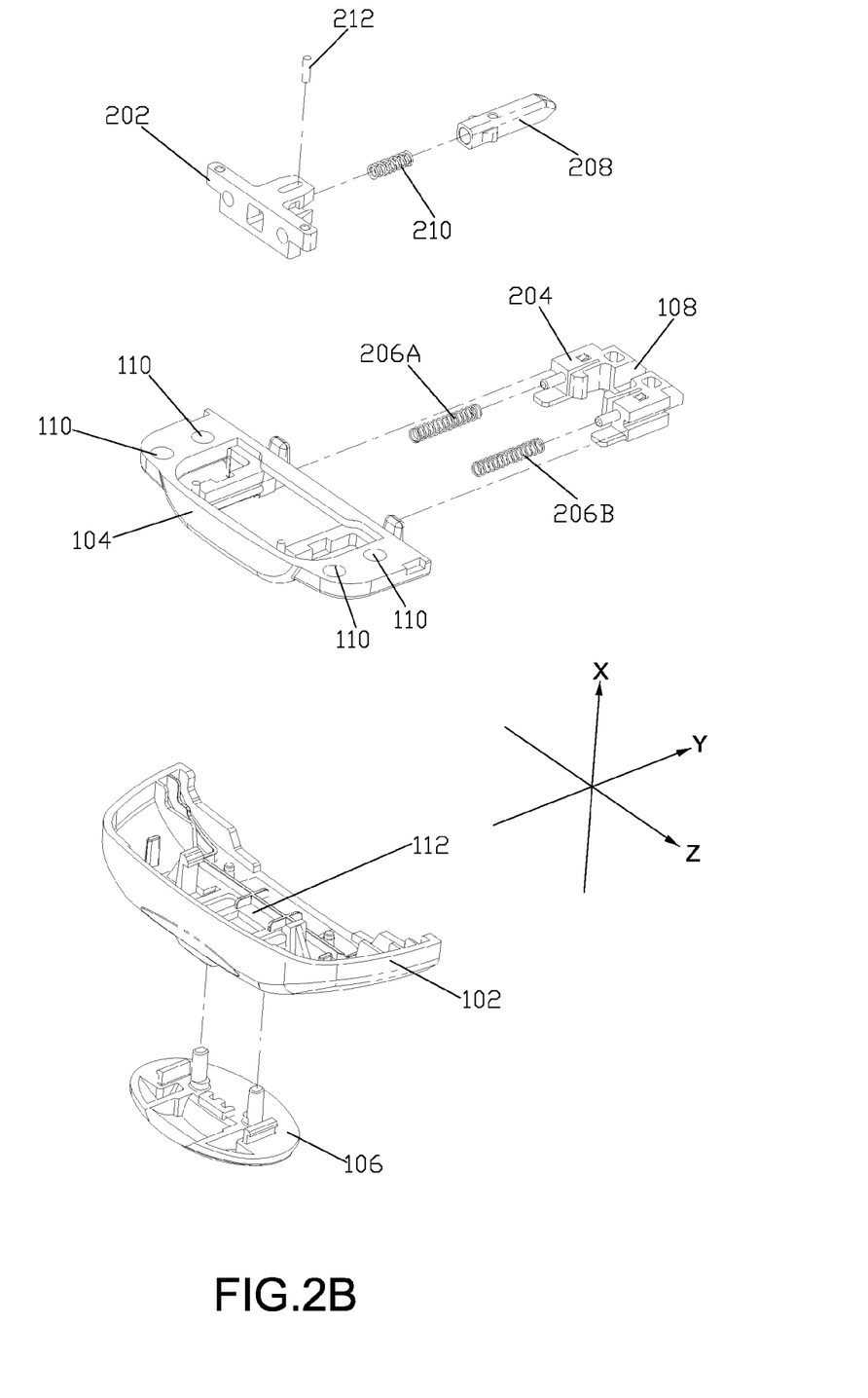

FIGS. 2A and 2B illustrate exploded views of latch 100 in one embodiment of the invention. Latch 100 can be mounted to the window sash through mounting holes 110 defined in base 104. Alternatively, cover 102 may include cantilevered hooks for snap fit onto the window sash. Cover 102 has a dust cover wall 112 that prevents particles from entering latch 100 and interfering with components of a latching mechanism mounted to base 104. Dust cover wall 112 also hides the components of the latching mechanism from view.

The components mounted to base 104 include a fixed plate 202, a latch head 204, latch head springs 206A and 206B, a plunger 208, a plunger spring 210, and a plunger pin 212. FIGS. 3, 4, 5, 6, 7, and 8 respectively illustrate cover 102, base 104, fixed plate 202, latch head 204, plunger 208, and trigger 106 in more detail.

Figure 3:
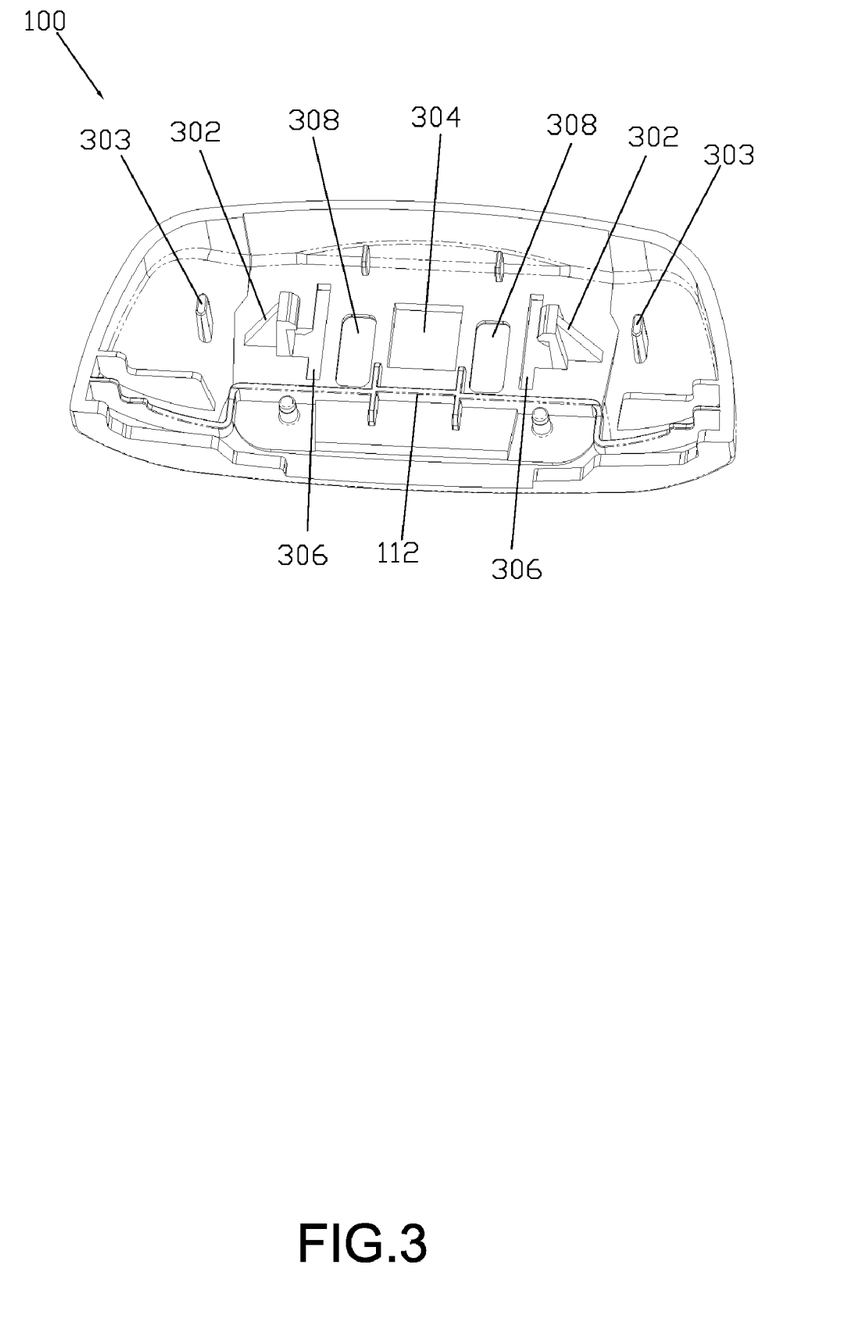
FIG. 3 is a perspective interior view of a cover of the latch of FIG. 2 in one embodiment of the invention.
Figure 4:
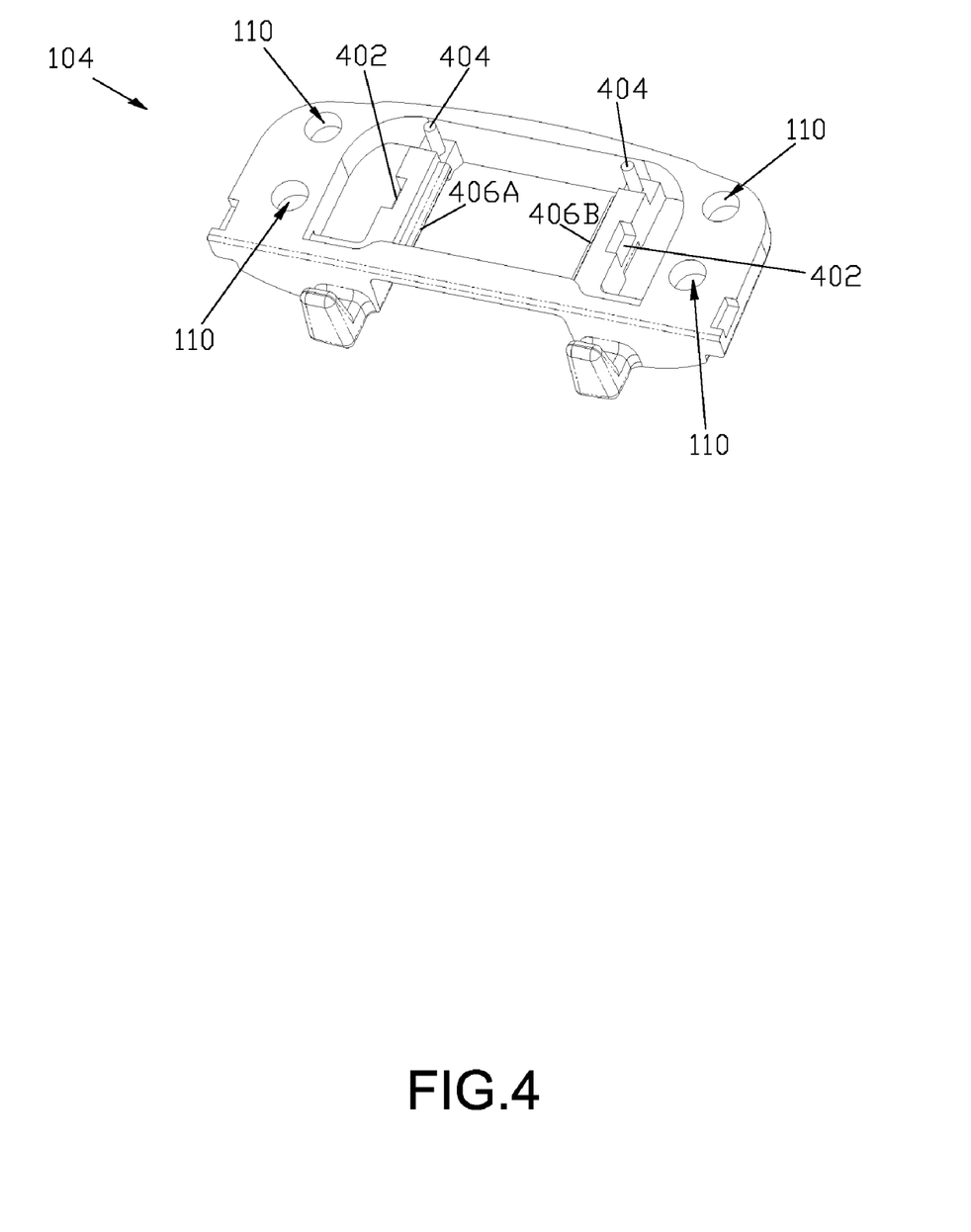
FIG. 4 is a perspective view of a base of the latch of FIG. 2 in one embodiment of the invention.

Referring to FIGS. 2, 3, and 4, cover 102 has cantilevered hooks 302 that engage grooves 402 of base 104 to snap fit the two components. Cover 102 also has posts 303 that prevent base 104 from tilting during assembly. Cover 102 may also include two posts below cantilevered hooks 302 to be inserted into corresponding holes in base 104.

Figure 5:
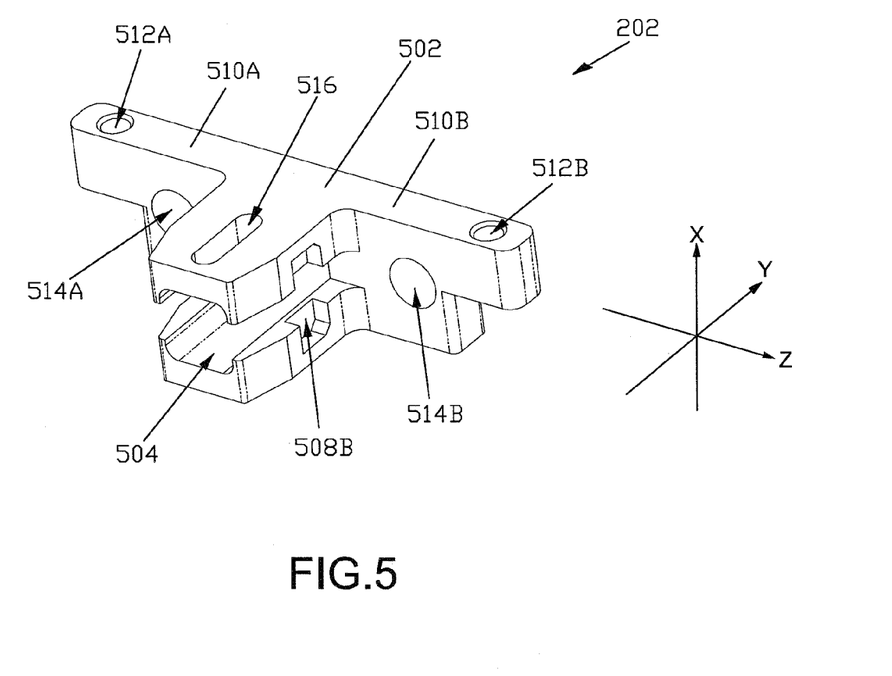
FIG. 5 is a perspective view of a fixed plate of the latch of FIG. 2 in one embodiment of the invention.
Figure 6:
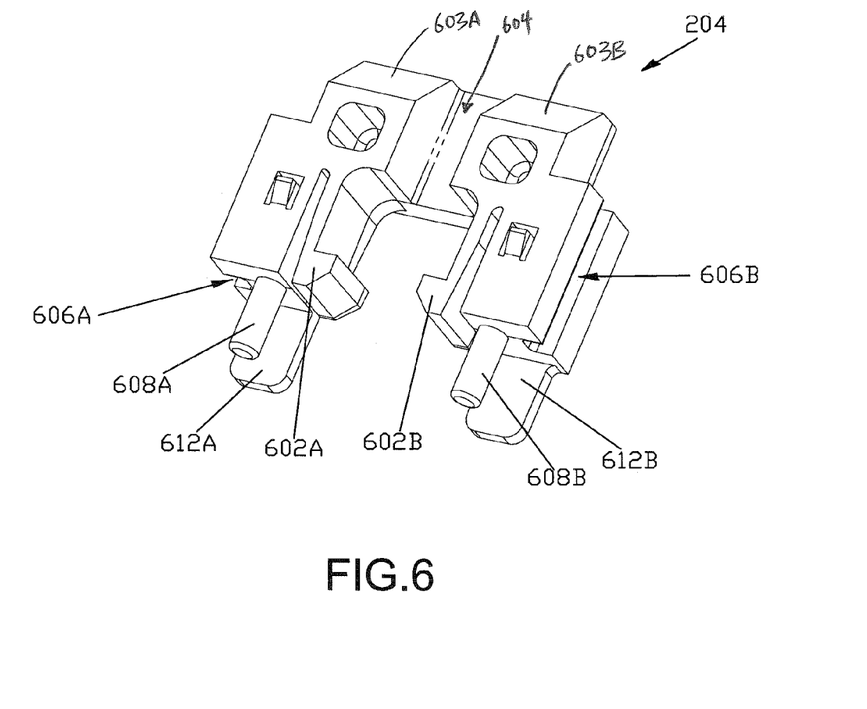
FIG. 6 is a perspective view of a latch head of the latch of FIG. 2 in one embodiment of the invention.

Referring to FIG. 5, fixed plate 202 has a central body 502 that defines a central passage 504 for receiving plunger 208 (FIG. 7), a guide slot 516 for receiving plunger pin 212 (FIG. 2), and notches 508A (FIG. 2) and 508B for engaging latch head 204 (FIG. 6).

Fixed plate further has distal ends 510A and 510B that extend from central body 502. Distal end 510A defines a mounting hole 512A along direction X and a spring hole 514A along direction Y. Symmetrically, distal end 510B defines a mounting hole 512B along direction X and a spring hole 514B along direction Y.

Referring to FIGS. 2, 4, and 5, fixed plate 202 is mounted to base 104 by inserting pins 404 of base 104 through mounting holes 512A and 512B of fixed plate 202.

Referring to FIG. 6, latch head 204 has two symmetrical halves with respective cantilevered hooks 602A and 602B for engaging notches 508A and 508B when latch head 204 is in a retracted position. The two halves have respective inclined faces 603A and 603B for contacting the strike. By having inclined faces 603A and 603B on only one side, latch head 204 can only contact the strike and retract when latch head 204 travels toward the strike.

Figure 8:
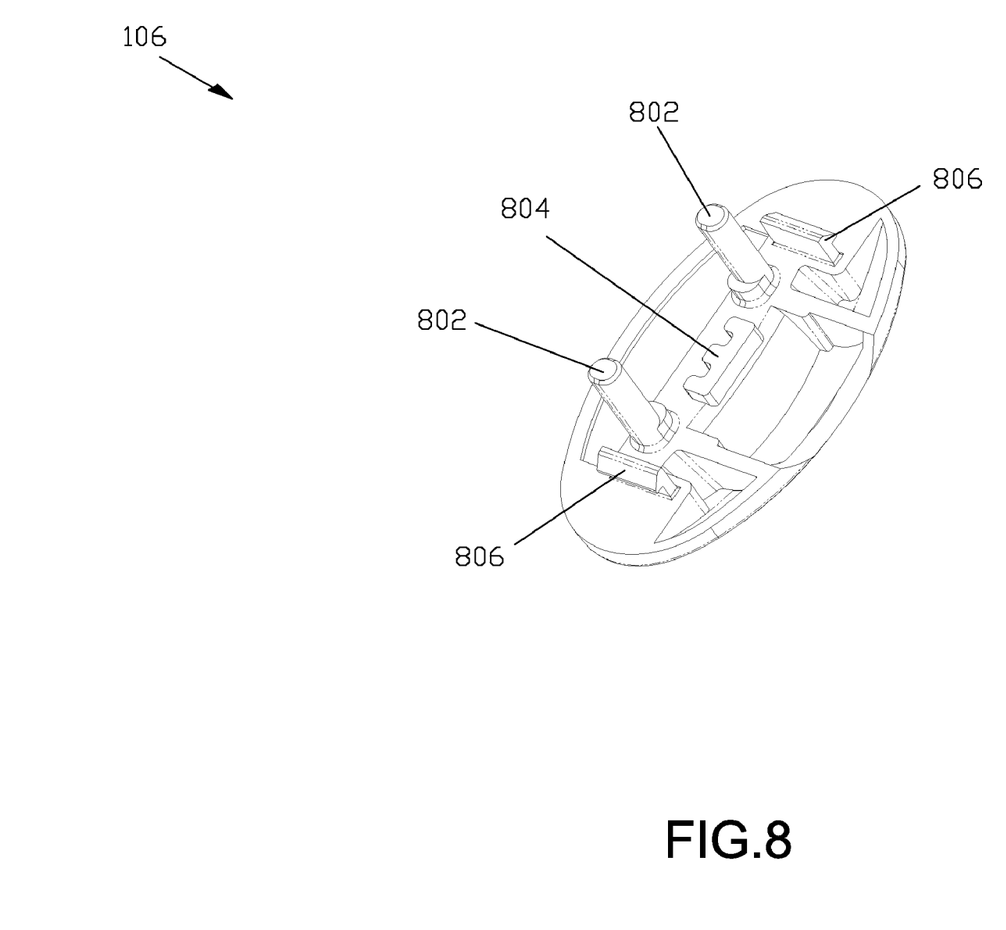
FIG. 8 is a perspective view of a trigger of the latch of FIG. 2 in one embodiment of the invention.

The two halves have vertical guide slots 606A and 606B for slidably engaging base 104 (FIG. 4). Vertical guide slots 606A and 606B allow latch head 204 to translate vertically relative to base 104 and fixed plate 202. Vertical guide slots 606A and 606B are centrally located on the respective surfaces they are formed in for added strength and stability. The two halves define a central passage 604 between faces 603A and 604B for receiving plunger 208 (FIG. 8). The two halves have respective pins 608A and 608B for engaging springs 206A and 206B. Holes 610 (FIG. 2A) are formed in latch head 204 to receive posts 802 of trigger 106 (FIG. 8). Respective plates or hoods 612A and 612B are formed behind pins 608A and 608B to protect springs 206A and 206B from misaligned posts 802 and other components during assembly.

Referring to FIGS. 2, 4, 5, and 6, the upper ends of springs 206A and 206B are inserted into respective spring holes 514A and 514B of fixed plate 202. Latch head 204 is then slid into base 104 by engaging guide slots 606A and 606B to guides 406A and 406B on base 104. At the same time, the lower ends of springs 206A and 206B are fitted around respective pins 608A and 608B of latch head 204 to spring load latch head 204 against fixed plate 202. Springs 206a and 206B symmetrically load latch head 204 so that latch head 204 translates in a smooth motion without any rotation.

Figure 7:
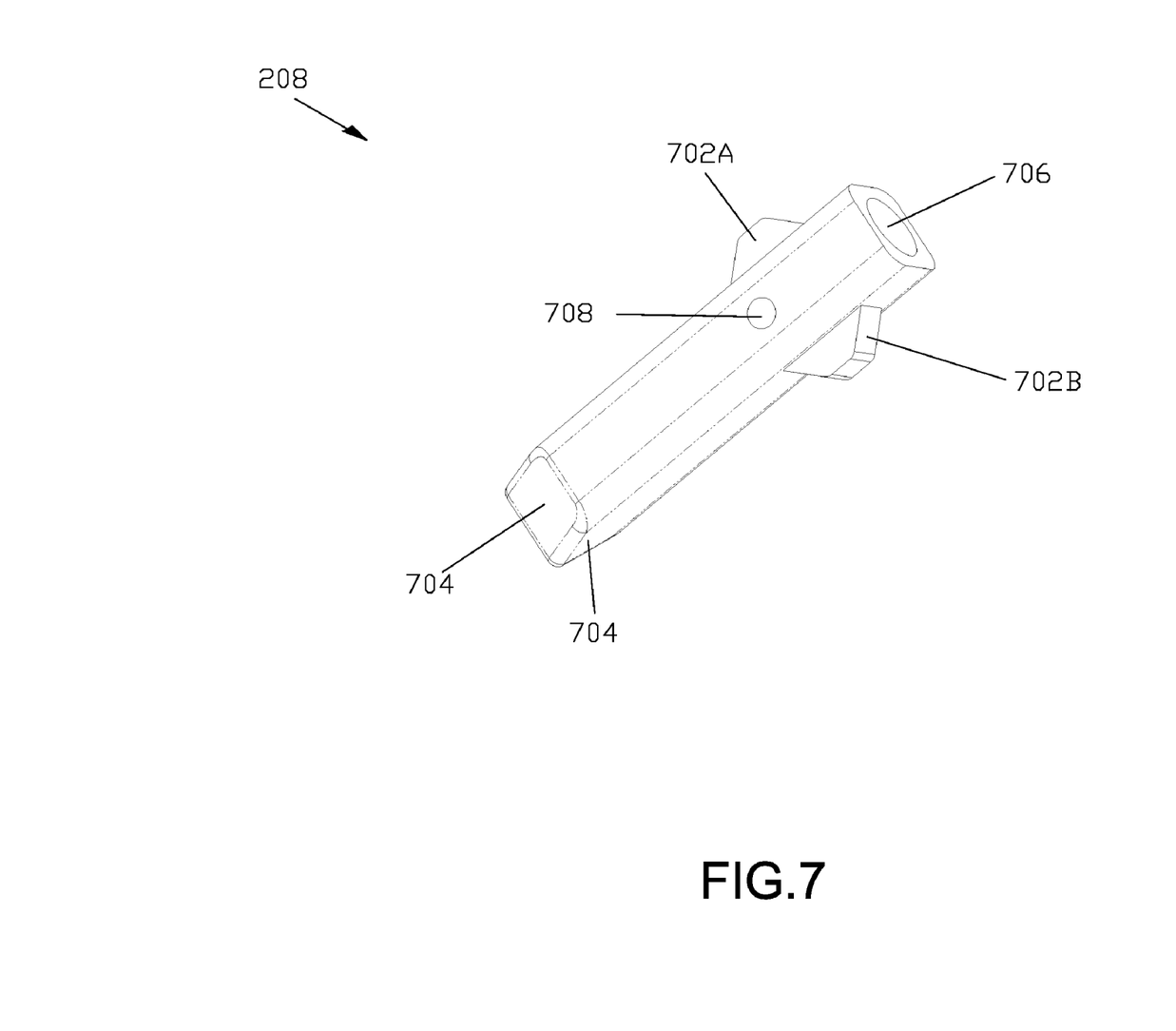
FIG. 7 is a perspective view of a plunger of the latch of FIG. 2 in one embodiment of the invention.

Referring to FIG. 7, plunger 208 has sloped shoulders 702A and 702B near the upper body of the plunger, and inclined faces 704 on both sides of the lower end of the plunger. By having inclined faces 704 on both sides, plunger 208 can contact the strike and retract when plunger 208 travels in either direction. Plunger 208 defines a spring hole 706 for receiving plunger spring 210, and a pin hole 708 for receiving plunger pin 212.

Referring to FIGS. 2, 5, 6, and 7, plunger spring 210 is inserted into spring hole 706 of plunger 208. Plunger 208 is inserted through passage 604 of latch head 204 and then passage 504 of fixed plate 202. As plunger 208 is centrally received in latch head 204, it does not cause latch head 204 to rotate and thereby contribute to the smooth movement of latch head 204.

Plunger pin 212 is inserted through guide slot 516 on fixed plate 202 and into pin hole 708 of plunger 208. Plunger pin 212 and guide slot 516 now guide and limit the vertical travel of plunger 208. Plunger spring 210 is pushed against a top wall of base 104 to spring load plunger 208.

Referring to FIG. 8, trigger 106 has posts 802 for coupling trigger 106 to latch head 204. Trigger 106 further has projection 804 and cantilever hooks 806 for mounting trigger 106 to cover 102.

Referring to FIGS. 2, 3, 6, and 8, trigger 106 is mounted to cover 102 by inserting projection 804 of trigger 106 into a guide slot 304 of cover 102, and by inserting hooks 806 into slots 306. Hooks 806 fix trigger 106 to cover 102 but allow trigger 106 to travel vertically. When mounted, posts 802 of trigger 106 pass through guide slots 308 on cover 102 and into pin holes 610 on latch head 204.

Figure 9:
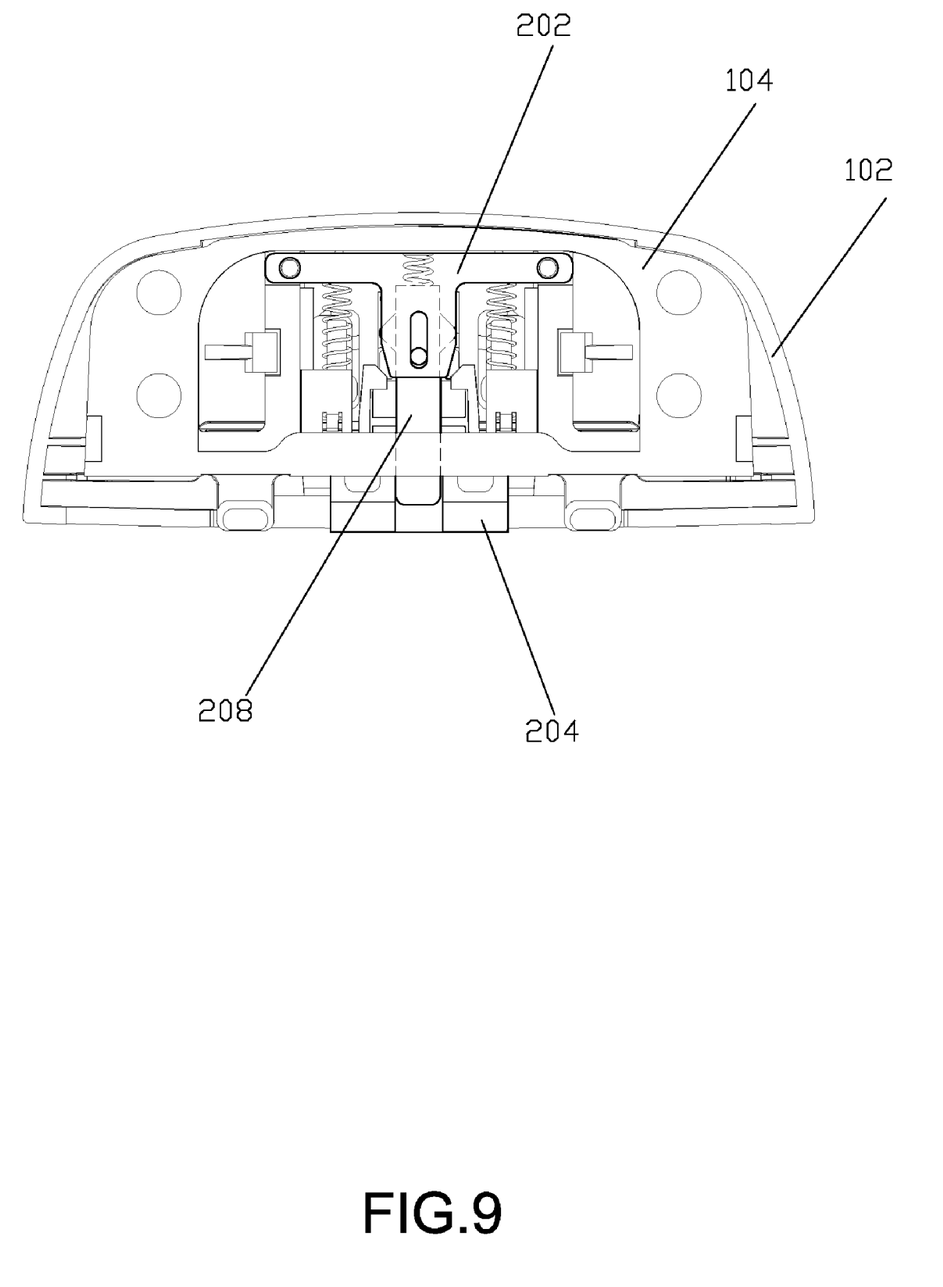
FIG. 9 is a back view of the latch of FIG. 1 with the latch head in its retracted position and the plunger in its extended position in one embodiment of the invention.

FIG. 9 illustrates a back view of latch 100 where latch head 204 and plunger 208 are both in their extended positions. When the window sash is almost closed against a window frame, the inclined faces of latch head 204 and plunger 208 contact the strike and latch head 204 and plunger 208 are pushed to their retracted positions.

When the window is fully closed and latch head 204 and plunger 208 clear the strike, latch head 204 and plunger 208 return to their extended positions and latch head 204 locks the window sash against the strike. Note that latch head 204 does not lock onto fixed plate 202 because latch head 204 and plunger 208 are moving in unison and shoulders 702A and 702B of plunger 208 prevent hooks 602A and 602B of latch head 204 from engaging notches 508A and 508B of fixed plate 202.

Figure 10:
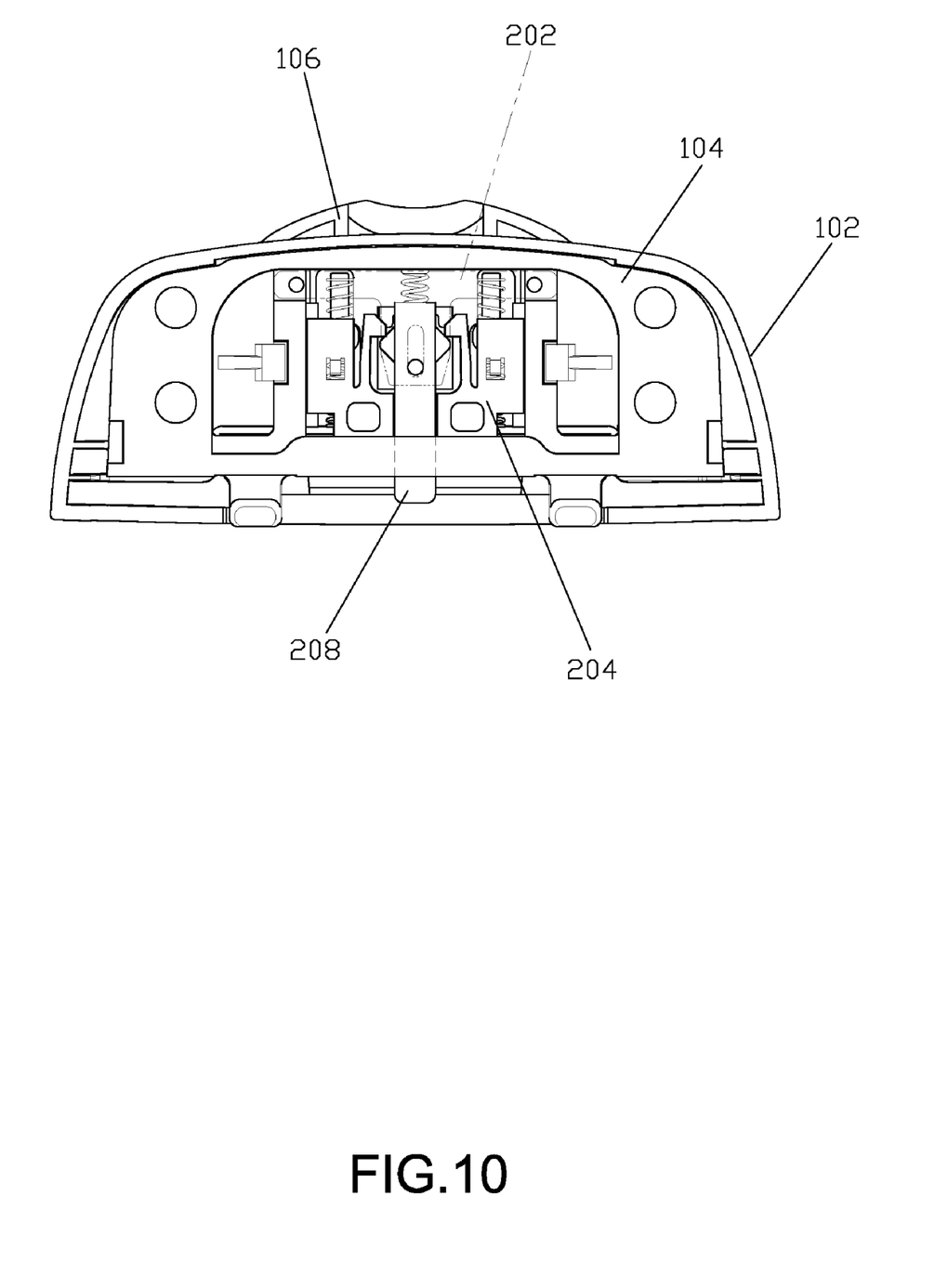
FIG. 10 is a back view of the latch of FIG. 1 with the plunger in a retracted position and the latch head in its extended positions in one embodiment of the invention.

When the user opens the window sash, the user pulls trigger 106 to retract latch head 204 toward fixed plate 202 so it will clear the strike. Once hooks 602A and 602B of latch head 204 engage notches 508A and 508B of fixed plate 202, latch head 204 is locked in a retracted position. This allows the user to use both hands to open the window sash. FIG. 10 illustrates a back view of latch 100 where latch head 204 is in its retracted position while plunger 208 remains in its extended position.

Figure 11:
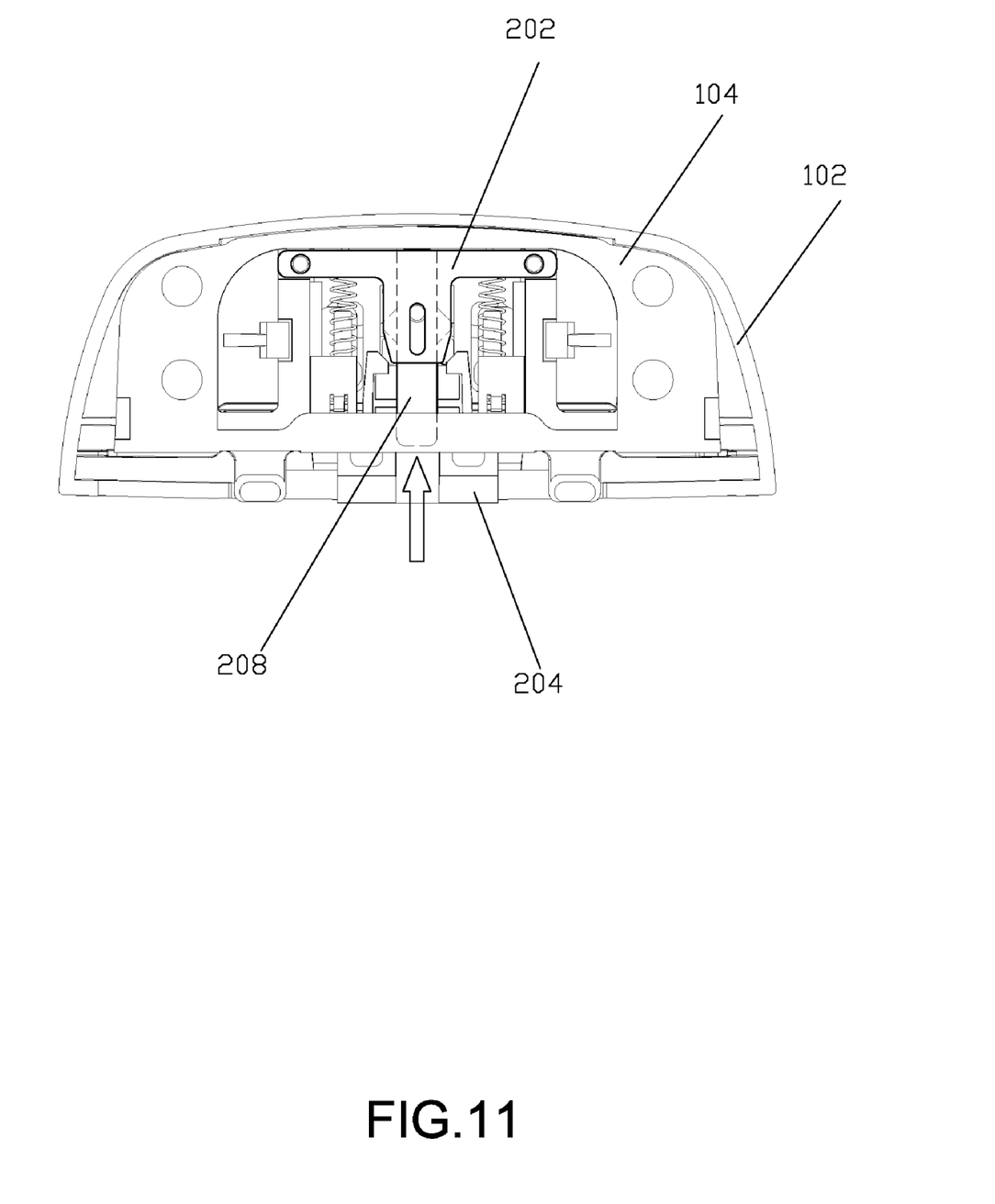
FIG. 11 is a back view of the latch of FIG. 1 with the latch head and the plunger in their extended positions in one embodiment of the invention.

As plunger 208 has angled faces 704 on both sides, it temporarily retracts and then returns to its extended position when the window sash opens. While retracting, shoulders 702A and 702B of plunger 208 releases hooks 602A and 602B of latch head 204 from notches 508A and 508B of fixed plate 202. This allows latch head 204 to return to its extended position as shown in FIG. 11 and ready to engage the strike the next time the window sash is closed.

Various other adaptations and combinations of features of the embodiments disclosed are within the scope of the invention.

The invention claimed is:

1. A latch for engaging a strike, the latch comprising:
   a base;
   a fixed plate mounted to the base, the fixed plate comprising a central body defining:
      a first passage accessible from at least one end of the central body;
      first and second slots on lateral sides of the central body, the first and the second slots being opened to the first passage; and
      first and second notches formed over the first and the second slots, respectively;
   an integral latch head for engaging the strike, the latch head comprising first and second halves defining a second passage centrally located in the latch head, the first half comprising a first hook, the second half comprising a second hook;
   first and second springs that symmetrically spring load the first and the second halves of the latch head, respectively;
   a plunger having a first end slidably received in the first passage and a second end slidably received in the second passage, the plunger comprising first and second shoulders received in the first and the second slots, respectively;
   a third spring that spring loads the plunger;
   wherein the latch head is locked in a retracted position when the latch head slides toward the fixed plate and the first and the second hooks engage the first and the second notches, respectively; and
   wherein the latch head is released in an extended position when the plunger slides toward the fixed plate and the first and the second shoulders push against the first and the second hooks, respectively, to disengage them from the notches.

2. The lock of claim 1, wherein the fixed plate further comprises first and second distal ends about the central body, the first distal end defining a first hole for receiving the first spring, the second distal end defining a second hole for receiving the second spring.

3. The latch of claim 2, wherein the first half of the latch head includes a first pin for engaging the first spring, and the second half of the latch head includes a second pin for engaging the second spring.

4. The latch of claim 3, wherein the plunger defines a third hole for receiving the third spring.

5. The latch of claim 4, wherein the base comprises guides for engaging guide slots on the latch head to control a translation of the latch head.

6. The latch of claim 5, wherein the central body defines a guide slot and the plunger defines a hole, the latch head further comprising a pin in the guide slot and the hole to control a translation of the plunger.

7. The latch of claim 6, wherein the base further comprises a first plurality of pins for engaging a first plurality of holes in the fixed plate.

8. The latch of claim 7, further comprising a cover mounted to the base.

9. The latch of claim 8, further comprising a trigger having a second plurality of pins passing through additional guide slots on the cover and received in a second plurality of holes on the latch head, wherein the trigger is translated to release the latch head from the strike.

10. The latch of claim 8, wherein the cover has cantilever hooks for mounting to the base, and posts that prevents the base from tilting during assembly.

11. The latch of claim 8, wherein the cover has a height that hides the strike.

12. The latch of claim 8, wherein the cover comprises a dust cover wall that prevents particles from entering into the latch.

13. The latch of claim 8, wherein the latch has a depth for mounting to a narrow check rail of the window.

14. A latch for engaging a strike, the latch comprising:
a base having guides;
a cover mounted to the base;
a fixed plate mounted to the base, the fixed plate having a central body and two distal ends, the central body defining a first passage, notches about the first passage, a guide slot, and first and second lateral side slots open to the first passage;
an integral latch head for engaging the strike, the latch head comprising two halves defining guide slots receiving the guides of the base, the two halves defining a second passage centrally located in the latch head, the two halves comprising hooks;
first and second springs between the two distal ends of the fixed plate and the two halves of the latch head for symmetrically spring loading the first and the second halves of the latch head;
a plunger having a first portion slidably received in the first passage and a second portion slidably received in the second passage, the plunger comprising two shoulders and defines a hole, the shoulders being received in the first and the second lateral side slots;
a pin in the guide slot of the central body of the fixed plate and the hole in the plunger to control a translation of the plunger;
a third spring between a top wall of the base and the plunger, the third spring loading the plunger;
wherein the latch head is locked in a retracted position when the latch head slides toward the fixed plate and the hooks engage the notches; and
wherein the latch head is released in an extended position when the plunger slides toward the fixed plate and the shoulders push against the hooks to disengage them from the notches.

* * * * *

UNITED STATES PATENT AND TRADEMARK OFFICE
CERTIFICATE OF CORRECTION

| | | |
|---|---|---|
| PATENT NO. | : 7,874,598 B2 | Page 1 of 1 |
| APPLICATION NO. | : 11/669166 | |
| DATED | : January 25, 2011 | |
| INVENTOR(S) | : Stanley Chung | |

It is certified that error appears in the above-identified patent and that said Letters Patent is hereby corrected as shown below:

Column 5,
Line 11, Claim 6, where "the latch head" should read --the latch--.

Signed and Sealed this
Twelfth Day of April, 2011

David J. Kappos
*Director of the United States Patent and Trademark Office*